United States Patent
Kraus et al.

(10) Patent No.: US 7,109,678 B2
(45) Date of Patent: Sep. 19, 2006

(54) HOLDING ARRANGEMENT HAVING AN APPARATUS FOR BALANCING A LOAD TORQUE

(75) Inventors: Martin Kraus, Hüttlingen (DE); Hartmut Gärtner, Oberkochen (DE); Martin Poxleitner, Königsbronn (DE); Michael Wirth, Aalen (DE); Alfons Abele, Scwäbisch Gmünd (DE); Roland Brenner, Wallhausen (DE); Norbert Sporer, Wielenbach (DE); Matthias Hähnle, Munich (DE)

(73) Assignee: Carl-Zeiss-Stiftung, Heidenheim (DE)

( * ) Notice: Subject to any disclaimer, the term of this patent is extended or adjusted under 35 U.S.C. 154(b) by 133 days.

(21) Appl. No.: 10/879,037

(22) Filed: Jun. 30, 2004

(65) Prior Publication Data

US 2004/0263102 A1 Dec. 30, 2004

(30) Foreign Application Priority Data

Jun. 30, 2003 (DE) .............................. 103 29 549
Feb. 20, 2004 (DE) ...................... 10 2004 008 381

(51) Int. Cl.
*F16M 13/00* (2006.01)
*G02B 21/00* (2006.01)

(52) U.S. Cl. ..................... 318/560; 318/568.11; 901/9; 901/48; 248/280.11; 700/279; 700/261; 359/382; 359/384

(58) Field of Classification Search ..................... None
See application file for complete search history.

(56) References Cited

U.S. PATENT DOCUMENTS

| | | | |
|---|---|---|---|
| 5,332,181 A | 7/1994 | Schweizer et al. | |
| 5,402,582 A | 4/1995 | Raab | |
| 5,492,296 A | 2/1996 | Biber | |
| 5,642,220 A | 6/1997 | Kleinberg et al. | |
| 5,667,186 A | 9/1997 | Luber et al. | |
| 6,050,530 A * | 4/2000 | Nakamura | 248/123.2 |
| 6,105,909 A * | 8/2000 | Wirth et al. | 248/123.2 |
| 6,129,319 A * | 10/2000 | Metelski | 248/123.2 |
| 6,145,403 A * | 11/2000 | Aschenbrenner et al. | 74/490.01 |
| 6,186,023 B1 * | 2/2001 | Nakamura et al. | 74/490.01 |
| 6,254,046 B1 * | 7/2001 | Biber | 248/287.1 |
| 6,471,165 B1 | 10/2002 | Twisselmann | |
| 6,592,086 B1 * | 7/2003 | Sander | 248/123.11 |
| 6,763,286 B1 * | 7/2004 | Metelski | 700/279 |
| 6,979,123 B1 * | 12/2005 | Barta et al. | 378/197 |
| 2002/0108874 A1 * | 8/2002 | Metelski | 206/316.1 |

* cited by examiner

*Primary Examiner*—Marlyn Fletcher
*Assistant Examiner*—Eduardo Colon Santana
(74) *Attorney, Agent, or Firm*—Walter Ottesen

(57) ABSTRACT

In a holding arrangement (101) for a medical-optical instrument (103), an electric motor is provided in a rotational joint (111, 119) to compensate a load torque occurring in this rotational joint. This electric motor is supplied with current in correspondence to a detected position of the rotational joint (111, 119). A current control curve required for this purpose is stored in a memory. This current control curve can be determined in that the rotational joints are deflected with the electric motor into predetermined positions and the current demand needed therefor is detected.

29 Claims, 9 Drawing Sheets

HOLDING ARRANGEMENT HAVING AN APPARATUS FOR BALANCING A LOAD TORQUE

CROSS REFERENCE TO RELATED APPLICATIONS

This application claims priority of German patent application nos. 103 29 549.6, filed Jun. 30, 2003, and 10 2004 008 381.9, filed Feb. 20, 2004, the entire contents of which are incorporated herein by reference.

FIELD OF THE INVENTION

The invention relates to a holding arrangement including a holding arrangement for a medical-optical instrument. The holding arrangement has at least one rotational joint and has an apparatus for balancing a load torque which is caused by the medical-optical instrument on the rotational joint.

BACKGROUND OF THE INVENTION

A holding arrangement of this kind is disclosed in U.S. Pat. No. 5,492,296. Here, an adjustable stand for a surgical microscope is described. The stand includes first and second rotational joints. An elastic energy store is assigned to each one of these rotational joints. The elastic energy store includes a torsion spring having a pretension which can be adjusted. The elastic energy stores generate a compensating torque which counters a load torque in the rotational joints caused by the surgical microscope accommodated on the stand.

U.S. Pat. No. 5,667,186 discloses a holding arrangement for a medical-optical instrument wherein motorically-adjustable balancing weights are provided in order to compensate load torques occurring at the rotational axes of the holding arrangement.

U.S. Pat. No. 5,642,220 discloses a holding arrangement for a medical-optical instrument wherein a linear spring unit or a gas pressure cylinder is provided for generating a counter torque to compensate load torques. The linear spring unit or the gas pressure cylinder operate on a lever arm. A desired compensating torque can be adjusted in that a point of application of the gas pressure cylinder or linear spring unit is varied.

U.S. Pat. No. 5,402,582 discloses a holding arrangement for accommodating a probe head for measuring workpieces. The holding arrangement includes a multi-joint carrier arm. Torsion springs are provided in the joints of the carrier arm. These torsion springs generate torques which counter the load torques in these joints.

U.S. Pat. No. 5,332,181 discloses a motorized stand having a surgical microscope as a holding arrangement for a medical-optical instrument. This stand has a support column which is supported on a stand base and can be rotated about a vertical axis. A multi-joint carrier arm is arranged on this carrier column and has four rotational joints with motorized drives. A control unit is assigned to these motorized drives. The control unit is connected to angular transducers which are arranged on the rotational joints. The desired position of a specific rotational joint is inputted to the control unit. The drives of the holding arrangement are then supplied with current in correspondence to the pregiven joint position of a rotational joint in order to move a specific carrier arm section on a rotational joint into a desired angular position.

U.S. Pat. No. 6,471,165 discloses a surgical microscope having a stand which has a motorically-adjustable pivot axis running essentially horizontally. A step motor is disposed in this pivot axis. The step motor is controlled by an operator-controlled element and a servo adjustment of the surgical microscope, which is accommodated on this axis, is made possible. Force sensors or torque sensors are provided in the operator-controlled element.

SUMMARY OF THE INVENTION

It is an object of the invention to provide a holding arrangement wherein an equilibrium state can be adjusted for the force-free movement of an instrument about a rotational joint with the instrument being accommodated on the holding arrangement. It is a further object to provide a servo-controlled movement of the instrument about this rotational axis.

According to a feature of the invention, the apparatus for compensating the load torque includes an electric motor which is combined with a detecting unit for detecting the position of the rotational joint and can be supplied with current in dependence upon a detected rotational joint position for generating a counter torque balancing the load torque. For this purpose, a control unit is provided which adjusts the required motor current. To compensate the load torque, the control unit assigns a value for the motor current to a detected rotational joint position value and this motor current is outputted to the electric motor and the motor current causes the electric motor to generate a counter torque which compensates the load torque applied to the rotational joint. In this way, a compactly configured holding arrangement is provided which can be motorically tilted and pivoted and is easily adaptable to the different configurations of a medical-optical instrument for torque compensation.

In a further embodiment of the invention, a brake is assigned to the rotational joint. In this way, it can be ensured that the holding arrangement is not moved when no current is supplied to the electric motor.

In a further embodiment of the invention, the electric motor is coupled to the rotational joint by means of a gear assembly. In this way, a precise adjustment of the equilibrium state is made possible in the holding arrangement.

In a further embodiment of the invention, the electric motor includes a drive axis which extends offset to a rotational axis of the rotational joint. In this way, space for connecting apparatus to the medical-optical instrument is provided in the holding arrangement and, it is, for example, possible to undertake an optical beam decoupling at the particular rotational axis.

In a further embodiment of the invention, the means for detecting the position of the rotational joint include an encoder of the electric motor or a position transducer. In this way, an instantaneous position of the rotational joint can be precisely determined.

In another embodiment of the invention, an electronic memory is assigned to the control unit of the electric motor wherein a curve is stored of the current as a function of the rotational joint position or a table having current values and rotational joint positions corresponding to each other. In this way, a rapid assignment of the required current value for a given position of the medical-optical equipment is ensured.

In another embodiment of the invention, at least two rotational joints are provided with means for compensating a load torque. In this way, it is made possible that a medical-optical device, which is accommodated on the holding arrangement, can be moved force-free in correspondence to several degrees of freedom of movement.

In a further embodiment of the invention, means for detecting a time-dependent change of the position of the rotational joint are provided in the holding arrangement. These means preferably detect a time-dependent change of the rotational joint position via a mathematical derivative of the determined rotational joint position as a function of time. The determined change of the rotational joint position is supplied as a control variable to a control loop which outputs a motor current for the electric motor on the rotational joint as a positioning quantity. This motor current is superposed on the motor current for torque compensation so that the motor generates an additional torque which counters a determined change of the rotational joint position.

With such a control loop, it is possible to simulate an inertial effect to an operator. Accordingly, for example, for a holding arrangement configured as a manipulator, it can be avoided that the trembling of a human hand is superposed on the instrument itself with the human hand guiding the instrument accommodated on the holding arrangement. At the same time, such a control loop makes possible that non-predefinable forces and torques are detected as a real touch feedback without falsifying external forces. These predefinable forces and torques are, in surgery, for example, cutting and return forces when cutting elastic tissue and when performing a resection or, other than surgery, when picking up an unknown item by the operator with a corresponding tool.

In the area of medicine, physicians, for example, are hereby placed in the position to keep their hands clear of a surgical area. This affords the possibility to utilize radiation-intensive intraoperative imaging methods during surgery and to be able to also treat highly infectious patients. Low vibration and precise movements can be carried out with a holding arrangement configured as a manipulator. For this reason, with the use of such a manipulator with a surgical microscope, a preparation intensive navigation is, as a rule, no longer necessary for a navigation utilized often for precise interventions.

With a corresponding active superpositioning of current curves or current control curves of several electric motors of the manipulator in the weight-equalized state, semi-robotic functions can be realized as required. For example, the user, with a suitable control, can be kept away from critical regions of the surgical area either entirely or he can be warned by an artificial resistance as long as the user wants this. For this purpose, the data of navigation tools, virtual 3D models or 3D tracks in the corresponding motor positions can be converted to additively superposed motor currents. In the area of surgery, it can be especially ensured that surgery takes place only in the peripheral region of a tumor.

Generally, the described control principle (open loop and/or closed loop) for a holding arrangement has the advantage compared to the classic robot technology that it needs no force sensors and/or no torque sensors and no complex sensor actuating control need be used, which is difficult to manage and with specific dynamic regions which are only accessible with difficulty.

If, in the holding arrangement, the mass distribution of the carrier arms is so selected that at least approximately a weight compensation about the rotational axis is provided for the particular joint, then comparatively weak motors can be used for shifting the holding arrangement. These motors must then only compensate slight torques. In a holding arrangement, whose carrier arms are balanced about the rotational axes of rotational joints, it would, for example, only be necessary that the motors compensate the torques caused in the rotational axis by a tool which is taken up in addition.

In a further embodiment of the invention, the medical-optical instrument is accommodated with a parallelogram arm on a carrier arm. Such a parallelogram arm makes it possible that the means for compensating a load torque can be ergonomically favorably mounted in the region of a stand arm above the medical-optical instrument. Furthermore, a stable accommodation of the medical-optical instrument on the holding arrangement is ensured in this way.

In a method for determining a current control curve for adjusting an equilibrium state in a holding arrangement of the invention, the following takes place: the at least one rotational joint is moved by means of the electric motor about an axis of the rotational joint; the current demand of the electric motor for moving the rotational joint is determined; the instantaneous position of the rotational joint is determined; and, the determined current demand in dependence upon the rotational joint position is stored in an electronic memory as a current control curve. In this way, an equilibrium state can be adjusted for the holding arrangement for different configurations of medical-optical equipment.

It is also possible to determine a current control curve in that the at least one rotational joint is moved by means of the electric motor in a first direction. The current demand of the electric motor, which is needed for moving the rotational joint, is determined in dependence-upon the position of the rotational joint and thereafter, the at least one rotational joint is moved by means of the electric motor in a second direction opposite to the first direction. The current demand of the electric motor, which is needed for the movement of the rotational joint, is determined in dependence upon the position of the rotational joint.

Preferably, a mean value of the current demand, which is needed for the movement of the at least one rotational joint in the first direction, and of the current demand, which is needed for the movement of the at least one rotational joint in the second direction, is computed and is stored in dependence upon the rotational joint position in an electronic memory as a current control curve. In this way, it is possible to generate a current control curve which is not burdened by errors which are caused by the friction forces in the particular rotational joint.

For the determination of the current control curve of the at least one rotational joint, it is sufficient to move the rotational joint with the electric motor over a rotational angular section $\Delta\Phi$, for example, $|\Delta\Phi| \leq \Pi$ or $|\Delta\Phi| \leq \Pi/2$ or $|\Delta\Phi| \leq \Pi/4$ because a conclusion can be drawn from a section of the detected current control curve as to the total course of the current control curve in the angular range $0 \leq \Phi \leq 2\Pi$ which corresponds to a complete revolution of the rotational joint. In this way, it is possible to take up a desired current curve or current control curve for the rotational joint within a short time, if needed, within a few seconds.

For the holding arrangement, an instantaneous position of the rotational joint is detected and the electric motor is supplied with current corresponding to a current control curve stored in a memory. In this way, an equilibrium state can be established for the medical-optical equipment in that a current value for torque compensation for the electric motor is assigned to a specific position of the rotational joint.

It is further also possible to determine an instantaneous change of the position of the rotational joint and to then output a current to the electric motor which counters the change of the position of the rotational joint.

If several rotational joints are provided in the holding arrangement, which rotational joints have apparatus for compensating a load torque with electric motors, an equilibrium state can be adjusted in that an instantaneous position of a first rotational joint is determined, an instantaneous position of a second rotational joint is determined and an electric motor, which is assigned to the first rotational joint, and an electric motor, which is assigned to the second rotational joint, are supplied with current corresponding to a two-dimensional current control curve stored in a memory. The current control curve assigns a corresponding current value for the torque compensation to the rotational joints corresponding to the specific instantaneous position of the rotational joints.

In order to determine a two-dimensional current control curve for the adjustment of an equilibrium state in a holding arrangement, the position of a first rotational joint is detected and, for a known position of the first rotational joint, a second rotational joint is moved about its axis by means of an electric motor assigned to the second rotational joint and then, the current requirement of the electric motor is determined which is needed for moving the second rotational joint. Thereafter, the instantaneous position of the second rotational joint is detected and the specific current requirement is stored in dependence upon the position of the second rotational joint in an electronic memory as a first current control curve. Thereafter, in a known position of the second rotational joint, the first rotational joint is moved about its axis by means of the assigned electric motor. The current demand of the electric motor, which is needed for the movement, is determined, the instantaneous position of the first rotational joint is determined and then, the determined current demand is stored as a second current control curve in an electronic memory in dependence upon the position of the second rotational joint.

Corresponding methods can be applied for adjusting the equilibrium state in a holding arrangement with three or more rotational joints in that suitable three-dimensional or multi-dimensional current control curves are determined for electric motors, which are assigned to the rotational joints, and are applied for driving the electric motors.

In a holding arrangement, which is configured as a manipulator, it must be ensured that, for each newly picked up instrument, tool or workpiece, either first a calibration of position-dependent motor currents is made or, for each taken-up item, corresponding identifications together with the absolute or additive position-dependent compensation motor current curves can be called up, for example, from an electronic memory. For this purpose, items, which are intended to be taken up by the holding arrangement, should be provided with an automatic identification via a barcode or a microchip. Furthermore, it is possible to apply the methods for tool identification, which are known from the manufacturing industry, such as for automatic supply devices for tool machines.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
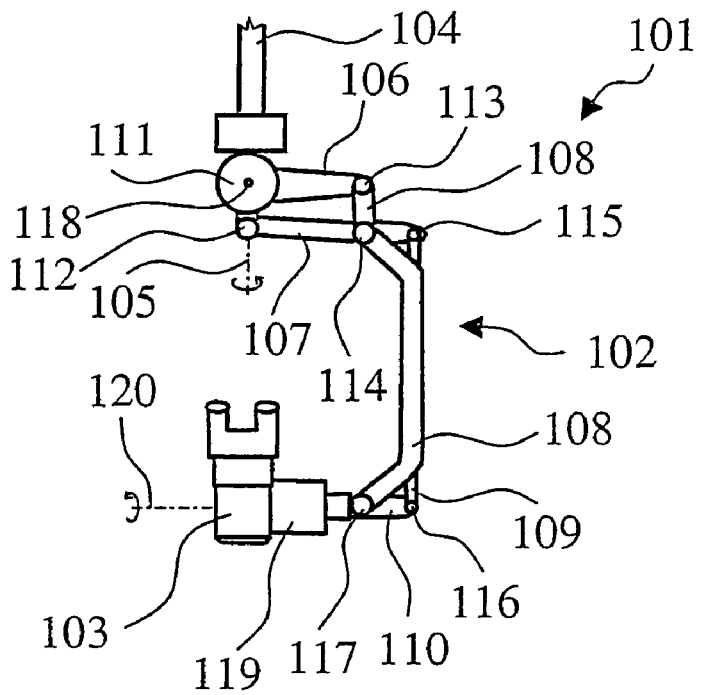
FIG. 1 shows a holding arrangement for a surgical microscope in a first position.

FIG. 1 shows a holding arrangement 101 having an articulated parallelogram arm 102 on which a medical-optical unit in the form of a surgical microscope 103 is accommodated. The holding arrangement 101 is attached to a stand (not shown) by means of a support guide 104. The holding arrangement 101 can be rotated about a vertical rotation axis 105 on this support guide 104.

The articulated parallelogram 102 includes parallelogram arms 106 to 110 having rotational joints 111 to 117. A first electric motor is assigned to the rotational joint 111. This electric motor makes possible a controlled movement of the articulated parallelogram 102 about a horizontal rotational axis 118. The surgical microscope is pivoted laterally with this movement.

A further rotational joint 119 having a rotational axis 120 is accommodated on the arm 110. An electric motor is also assigned to rotational joint 119. With this electric motor, a tilt movement of the surgical microscope 103 can be controlled about the rotational axis 120.

Figure 2:
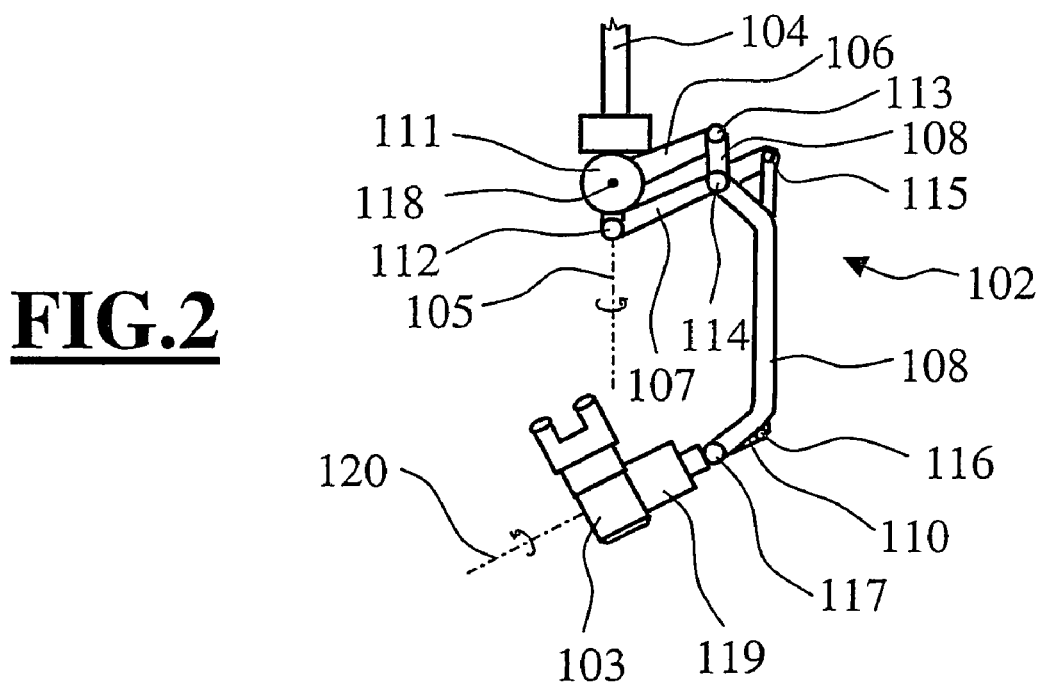
FIG. 2 shows the holding arrangement of FIG. 1 in a second position.

FIG. 2 shows the holding arrangement 101 of FIG. 1 in a deflected parallelogram position. The units of the holding arrangement are identified by the same reference numerals used in FIG. 1. The surgical microscope 103 in FIG. 2 is pivoted laterally relative to the position of the surgical microscope in FIG. 1.

Figure 3:
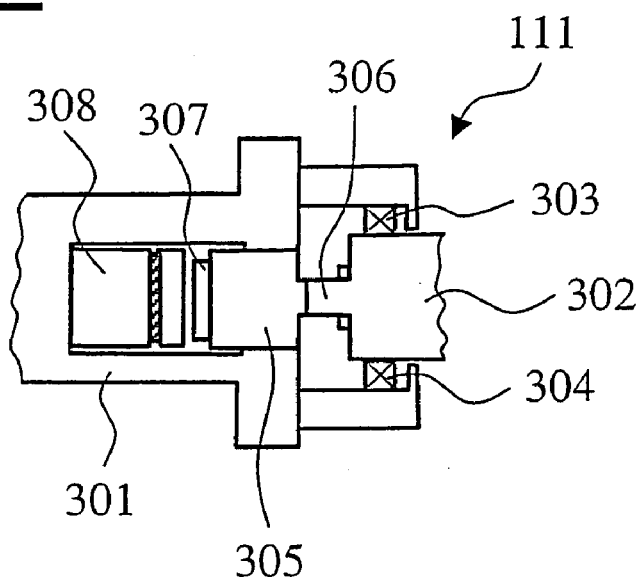
FIG. 3 is a schematic of a first rotational joint of the holding arrangement of FIG. 1.

FIG. 3 schematically shows the rotational joint 111 of holding arrangement 101 of FIG. 1. The rotational joint 111 has a first joint part 301 and a second joint part 302 which can be moved relative to joint part 301. The joint part 302 is journalled on the joint part 301 with support units 303 and 304. An electric motor 305 is assigned to the rotational joint 111 which is connected to the joint part 302 by means of a shaft 306. A torque can be generated with the electric motor 305-which is introduced into the second joint part 302 of the rotational joint 111.

The electric motor 305 has an encoder 307. This encoder 307 makes a voltage signal available from which, with a suitable signal processing unit, an instantaneous position of the electric motor and therefore of the shaft 306 can be derived. The position of the rotational joint 111 can therefore be determined from the voltage signal of the encoder 307.

In the rotational joint 111, a magnetic brake 308 is provided which, dependent upon the drive, enables or disables a movement of the second joint part relative to the first joint part.

With the torque, which the electric motor 305 provides, either a load torque, which is applied to the second joint part 302, can be compensated or the joint part 302 can be moved in correspondence with the drive of the electric motor 305.

Figure 4:
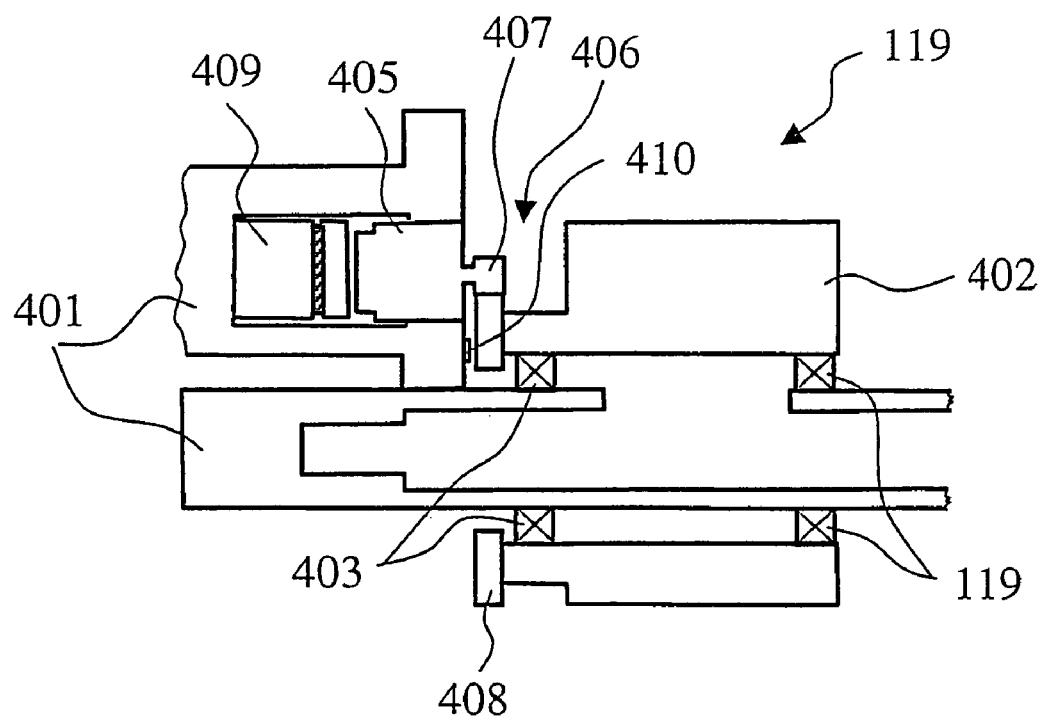
FIG. 4 is a schematic of a second rotational joint of the holding arrangement of FIG. 1.

FIG. 4 schematically shows the further rotational joint 119 of FIG. 1. As with rotational joint 111, an electric motor 405 is also assigned to the rotational joint 119 with which a torque, which is applied to the joint part 402, can be compensated. The electric motor 405 is held in a first joint part 401 of the rotational joint 119. The rotational joint 119 further includes support units 403 and 404 which make possible a movement of the second joint part 402 relative to the first joint part 401.

The electric motor 405 is coupled via a gear assembly 406 to the second joint part 402. This gear assembly includes a drive pinion 407 which is arranged on the drive shaft of the electric motor 405. This drive pinion 407 meshes with a toothed gear 408 which is fixedly connected to the second joint part.

In order to be able to enable or disable a movement of first joint part 401 and second joint part 402 even for an electric motor without current, a magnetic brake 409 is provided in the rotational joint 119.

The rotational joint 119 further includes a position transducer 410 which makes available a voltage signal which corresponds to an instantaneous position of the toothed gear 408 on the second joint part 402 of the rotational joint 119.

It will now be explained with respect to FIGS. 5 to 7 how a load torque, which occurs at the rotational joints 111 or 119 of FIG. 1, can be compensated with the electric motor in the rotational joints.

Figure 5:
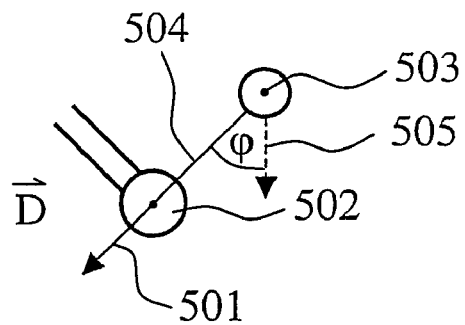
FIG. 5 shows how a rotational torque occurs in a rotational joint of the holding arrangement of FIG. 1.

For this purpose, FIG. 5 shows schematically a torque 501 which occurs on a rotational joint 502 because of a load having the centroid 503 which is taken up at the rotational joint 502 with the lever arm 504 because this load is subjected to a weight force 505. As a function of the angle $\Phi$ between the weight force 505 and the lever arm 504, there results a dependency of the magnitude of the torque $\vec{D}$ occurring at rotational joint 502 which is shown in FIG. 6.

The following equation applies: $\vec{D}=LMg \sin \Phi$ wherein:

L is the length of the resulting lever arm;

M is the mass of the centroid;

g is the acceleration of gravity constant; and, $\Phi$ is the angle between the lever arm and the direction of the weight force.

An equilibrium state is adjusted at the rotational joints 111 and 119 in that the electric motor in the rotational joints of the holding arrangement 101 of FIG. 1 is so supplied with current that it compensates a load torque occurring at the rotational joints.

Figure 7:
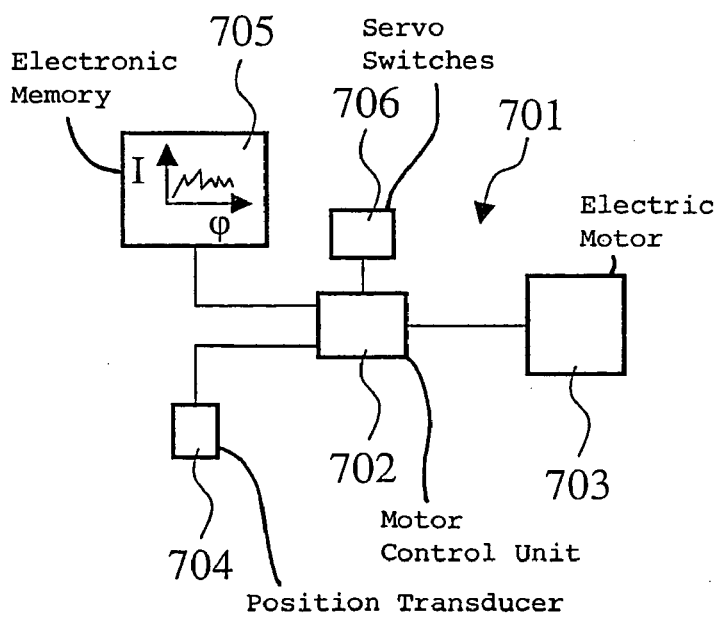
FIG. 7 shows a circuit arrangement for controlling an electric motor in a rotational joint of the holding arrangement of FIG. 1.

For automatically adjusting such an equilibrium state, the electric motors in these rotational joints are switched in correspondence to a circuit arrangement shown in FIG. 7. The circuit arrangement 701 includes a motor control unit 702 which is connected to the electric motor 703. Signals from a position transducer 704 are supplied to the motor control unit 702. The position transducer 704 is configured as an angle sensor or as an encoder. This position transducer 704 outputs an instantaneous angle position of the rotational joint. Corresponding to an instantaneously detected angle position of the rotational joint, a current control curve is read out which is stored in an electronic memory 705. This current control curve corresponds to the current value, which is required in each position of the rotational joint, for torque compensation by the electric motor.

Accordingly, if the position of the surgical microscope 103 of FIG. 1 is so changed that the rotational joints 111 or 119 are moved by the electric motors, then the corresponding motor control unit controls the motor current in correspondence to the instantaneous rotational joint positions in such a manner that a torque balance occurs in the rotational joints. For this purpose, a current control curve, which is stored in the particular electronic memory, is read out for each rotational joint (111, 119). This current control curve is dependent upon the positions of the two rotational joints (111, 119) and on the mass distribution of the medical-optical instrument taken up at the corresponding holding arrangement. If the mass distribution is changed, for example, in that a peripheral apparatus is connected to the medical-optical instrument, then a modified current control curve must be accessed for the torque compensation in the rotational joints.

Such a current control curve can basically be determined in a simple manner. For this purpose, the current, which is needed for moving the holding arrangement about the particular rotational joints by means of electric motors, is detected as a function of the instantaneous positions of these rotational joints and is stored in the particular electronic memory. For example, the rotational joint 111 is moved into a known position and, thereafter, the current control curve for the rotational joint 119 is recorded. In a next step, the rotational joint 119 is moved into a known-position and the corresponding current control curve for the rotational joint 111 is determined. From the current curve determined in this manner, a two-dimensional set of current data for compensation in each position of the rotational joints 111 and 119 can be determined by means of trigonometric functions.

Servo switches 706 are assigned to the motor control unit 702 in order to make possible a servo operation of the electric motor 703 for a rotational joint of the described holding arrangement. Such a servo operation can, for example, be of advantage for a fine adjustment of the medical-optical instrument on the holding arrangement.

Figure 8:
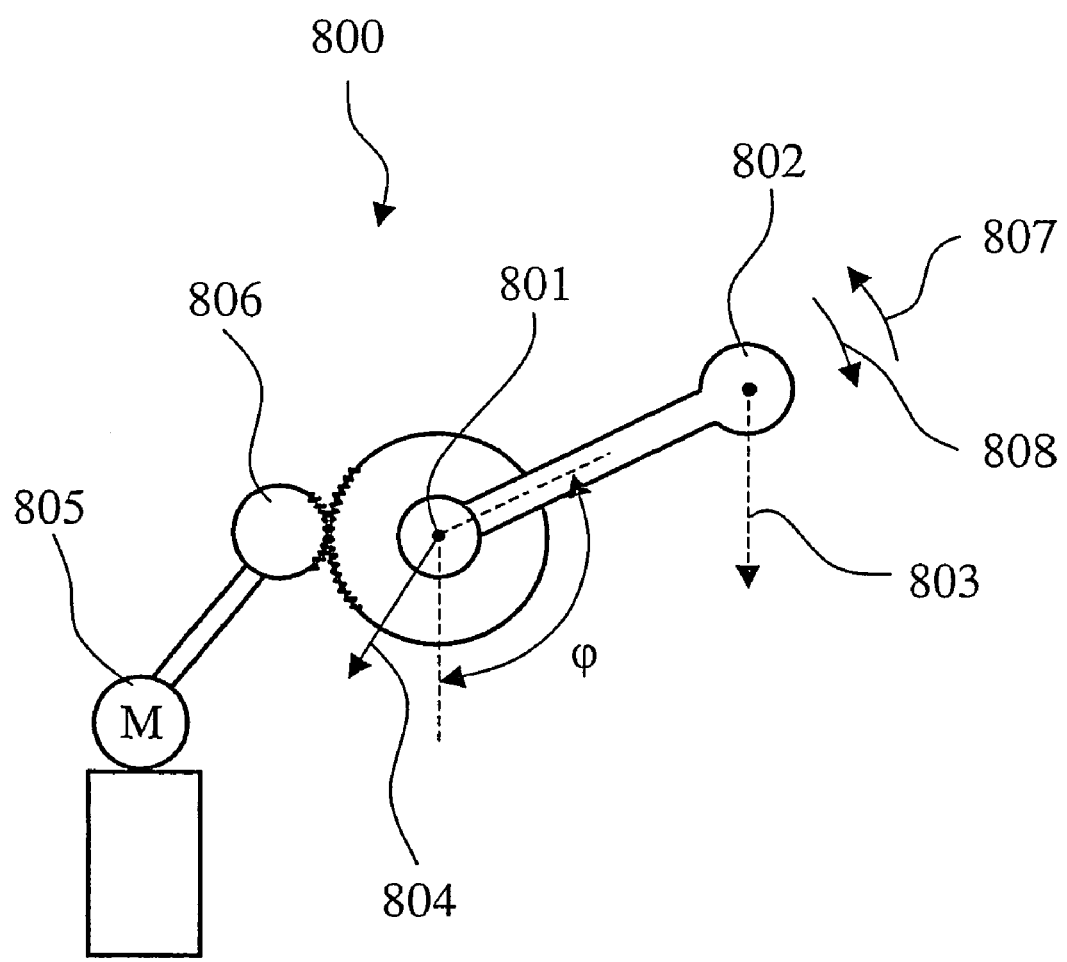
FIG. 8 is a schematic of a rotational joint having a medical-optical instrument and an electric motor.
Figure 9:
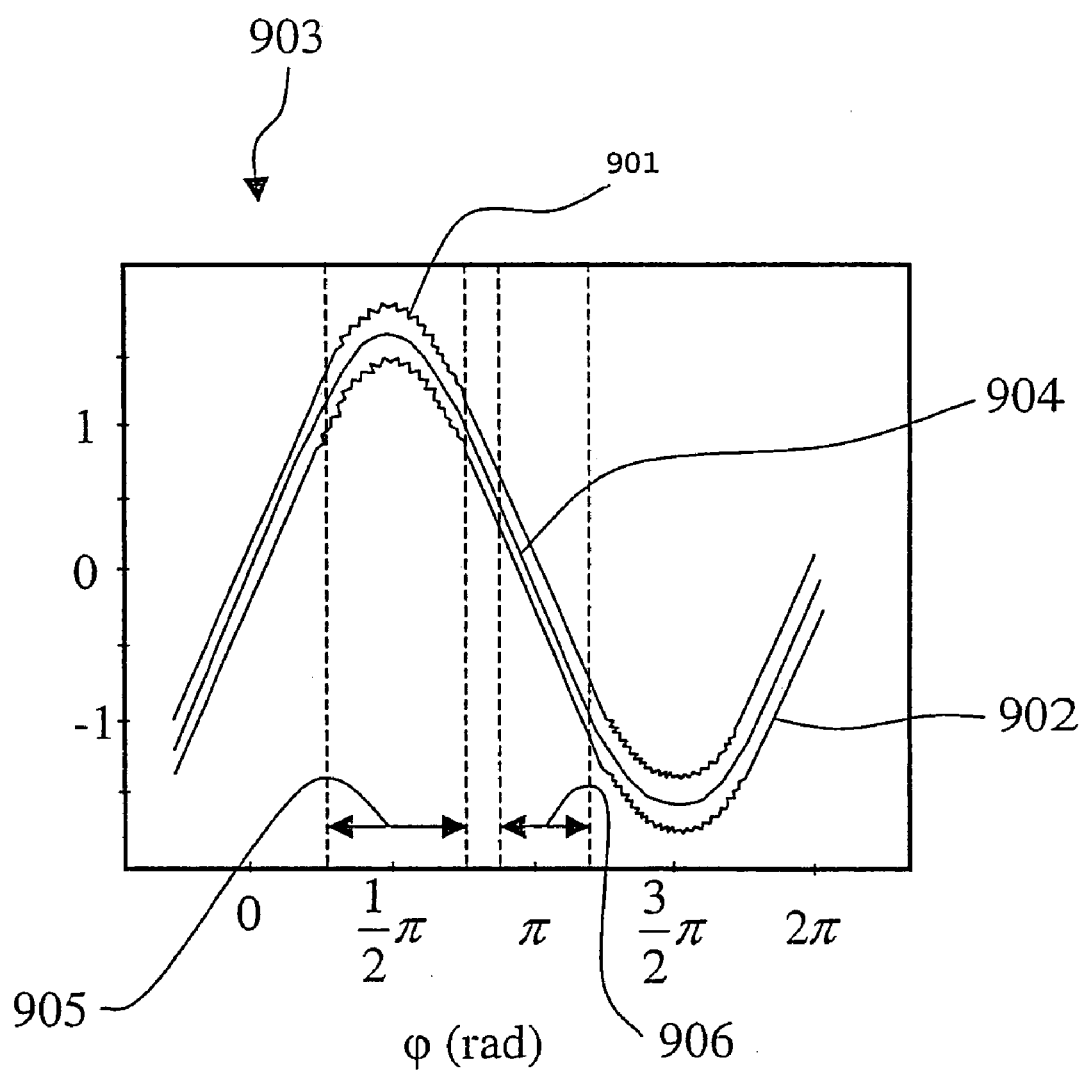
FIG. 9 shows motor current curves of the electric motor in the rotational joint of FIG. 8.

In FIGS. 8 and 9, a further method is described for determining a current control curve for torque compensation at a rotational joint of a holding arrangement.

FIG. 8 shows a rotational joint 800 of a holding arrangement which supports a mass, which is rotatably journalled about an axis 801, in the form of a medical-optical instrument 802. The medical-optical instrument 802 is subjected to a gravity force in the direction of arrow 803. This gravity force causes a load torque 804 in the axis 801 of the rotational joint 800. To compensate this load torque 804, a drive unit having electric motor 805 is assigned to the rotational joint 800. The electric motor 805 is coupled to the axis 801 of the rotational joint by means of a gear assembly 806 and can so move the medical-optical instrument 802 in the direction of arrows (807, 808). For a movement of the medical-optical instrument 802, friction forces and acceleration forces in general occur at the rotational joint 800.

These forces are especially dependent upon the direction in which the medical-optical instrument 802 is displaced at the rotational joint 800.

FIG. 9 shows, in a graph 903, a first motor current curve 901 for a motor current for the electric motor 805 of FIG. 8 as a function of the angular position $\Phi$ of the rotational joint 800 of FIG. 8 in order to move the medical-optical instrument 802 in the direction of the arrow 807. A motor current curve 902 corresponds to the motor current of the electric motor 805 of FIG. 8 which is necessary to move the medical-optical instrument in the direction of arrow 803 of FIG. 8.

The motor current curves 901 and 902 have noise caused by measuring operations and are displaced parallel to the abscissa of the graph 903. A non-noisy motor current curve 904 results from the formation of a mean value of the motor current curves 901 and 902 by means of suitable mathematical averaging algorithms. This motor current curve 904 corresponds to a torque at rotational joint 800, which can be generated by means of electric motor 805 of FIG. 8 and which, for a given rotational joint position, makes possible an exact static torque compensation. This motor current curve is neither made erroneous by friction forces nor by acceleration forces because the contribution of these forces are eliminated by the formation of the corresponding mean value.

In order to compute a suitable motor current curve for torque balancing, it is not necessary to move the medical-optical instrument 802 on the rotational joint 800 of FIG. 8 in the angular range $0 \leq \Phi \leq 2\Pi$ about the axis of the rotational joint 801.

Figure 6:
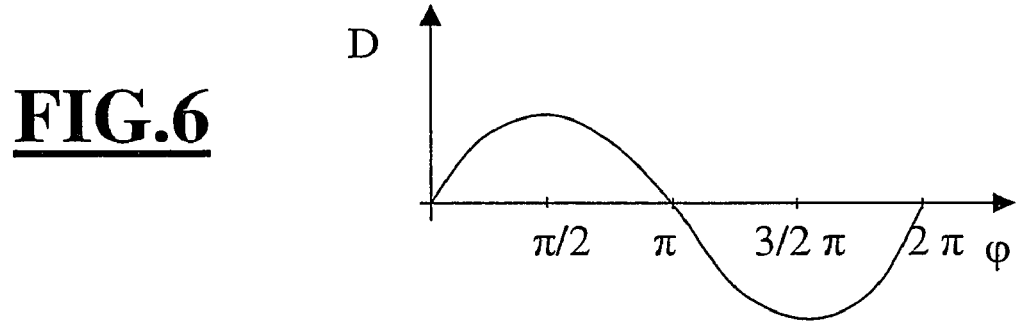
FIG. 6 shows the interrelationship between rotational joint position and a torque occurring at the particular rotational joint.

Since it is known that the static load torque in the rotational joint satisfies the relationship explained with respect to FIG. 6, it is possible by means of suitable mathematical algorithms to draw a conclusion as to a motor current curve in the angular range $0 \leq \Phi \leq 2\Pi$ from the detected course of the motor current curves in an angular range 905 or 906 in FIG. 9.

Figure 10:
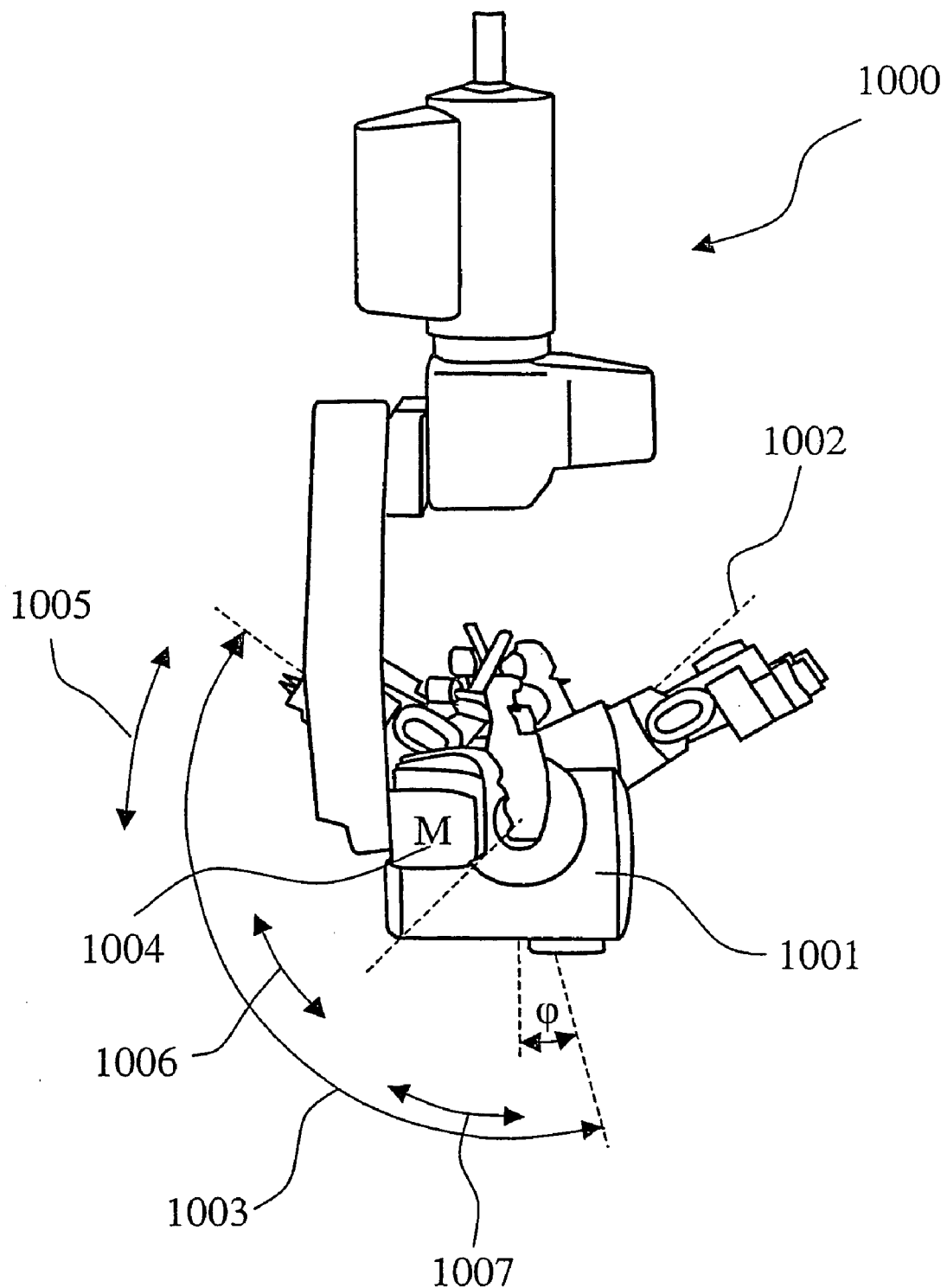
FIG. 10 shows a holding arrangement with a surgical microscope.

FIG. 10 shows a surgical microscope 1001 taken up on a holding arrangement 1000. The surgical microscope 1001 is rotatably journalled on the holding arrangement 1000 about an axis 1002 and can be displaced in the angular range indicated by the arrow 1003. To balance load torques at desired angular positions of the surgical microscope 1001, an electric motor 1004 is provided which operates on the surgical microscope 1001 by means of a gear assembly.

To record a suitable motor current curve for torque compensation, it is here sufficient to move the surgical microscope 1001, for example, over one of the angular ranges indicated by the arrows 1005, 1006 or 1007. In this way, and even when a movement of the surgical microscope 1001 about the axis 1002 is restricted because of connected ancillary apparatus, a fitting or suitable motor current curve for torque compensation can be determined over the entire accessible angular range.

Figure 11:
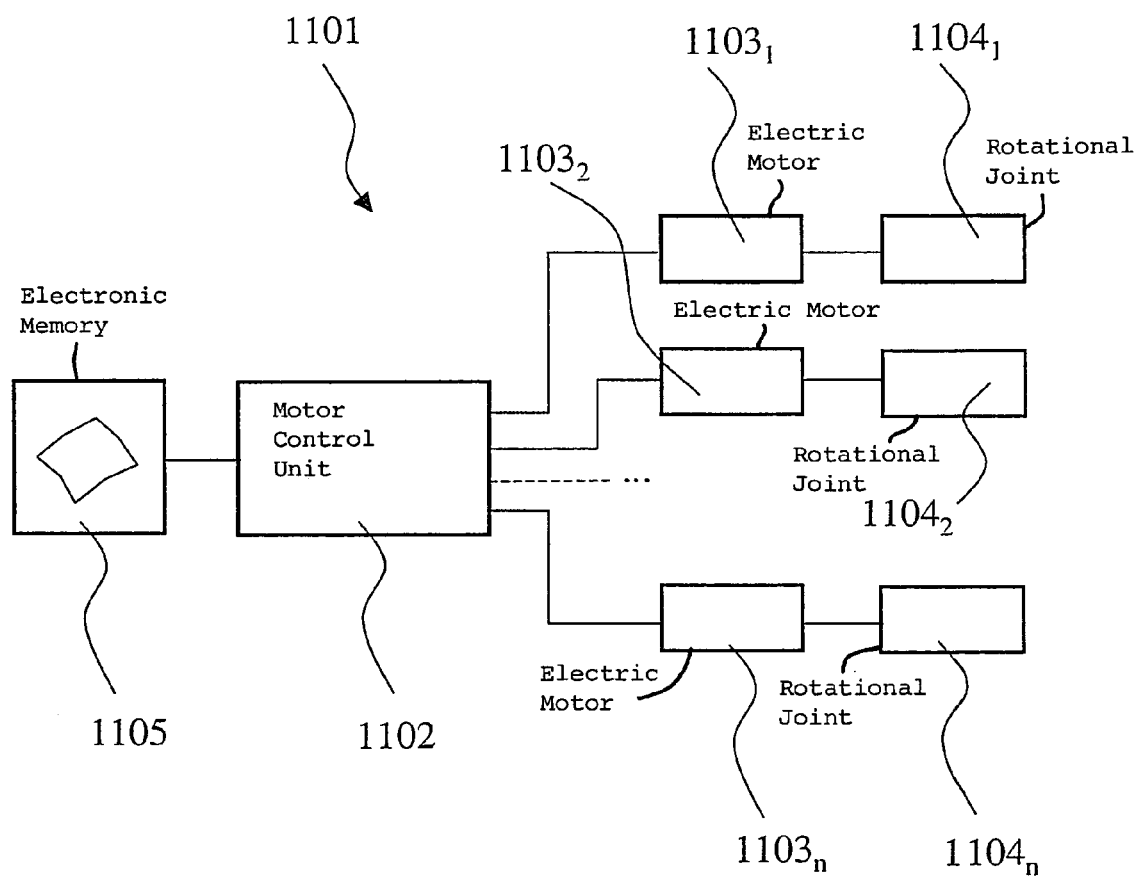
FIG. 11 is a schematic of a circuit arrangement for controlling several electric motors in a circuit arrangement having several rotational joints.

FIG. 11 is a schematic of a circuit arrangement for controlling several electric motors in a circuit arrangement having several rotational joints. The circuit arrangement 1101 has a motor control unit 1102 which is connected to electric motors $1103_1$, $1103_2$, ... $1103_n$. These electric motors $1103_1$, $1103_2$, ... $1103_n$ are assigned to rotational joints $1104_1$, $1104_2$, ... $1104_n$. Each of the rotational joints having an electric motor includes a position transducer or encoder with which the instantaneous angular position of the rotational joint can be determined. A multi-dimensional current control curve can be determined in that, first, the respective angular positions of all rotational joints $1104_1$, $1104_2$, ... $1104_n$ are determined. The multi-dimensional current control curve can be applied as the basis for adjusting an equilibrium in a holding arrangement having multiple rotational joints. In the known position of the rotational joints $1104_1$, ... $1104_n$, a current control curve as shown in FIG. 7 is recorded for the electric motor $1103_1$ of the rotational joint $1104_1$ and is stored as an n-dimensional data set in an electronic memory 1105. Thereafter, a corresponding current curve is recorded for the rotational joint $1104_2$ at known positions of the remaining rotational joints, et cetera.

After the determination of a current curve set, a current data set can be computed via conversion with corresponding trigonometric functions for all rotational joints $1104_1$, $1104_2$, ... $1104_n$ at known angular positions of all rotational joints. The current data set provides a current for equilibrium for each electric motor $1103_1$, $1103_2$, ... $1103_n$.

Figure 12:
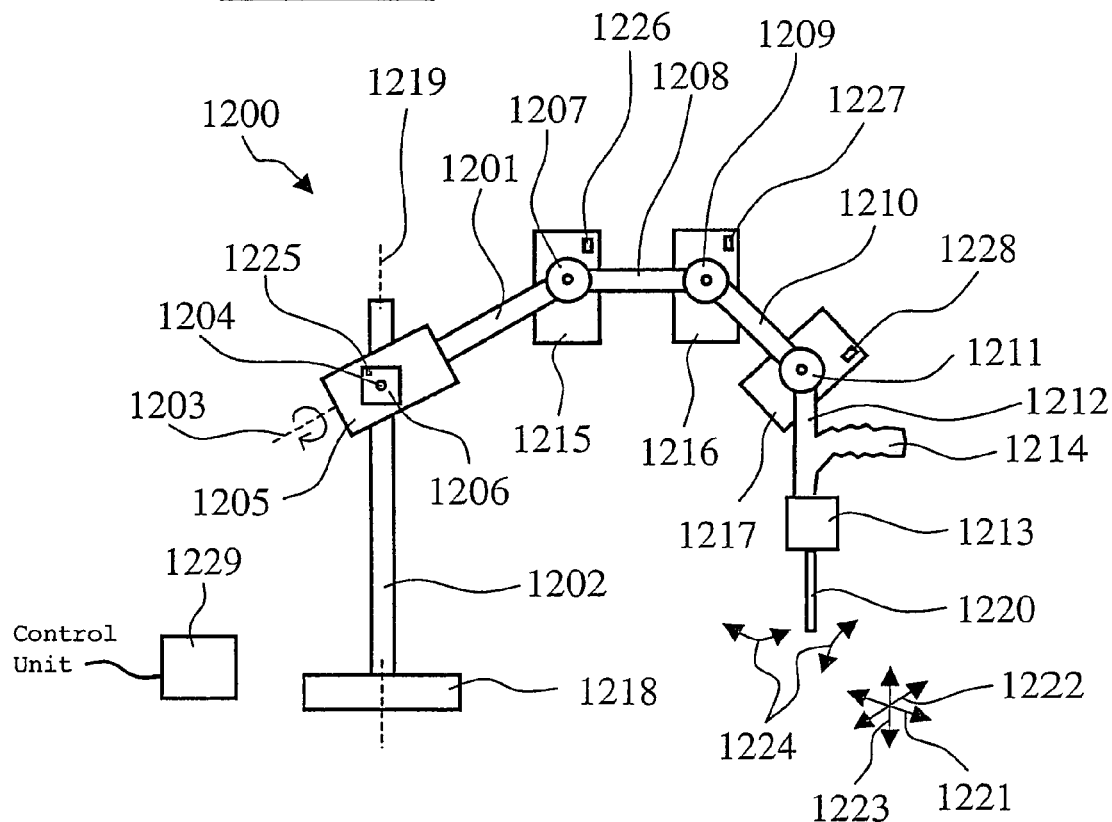
FIG. 12 is a schematic of a holding arrangement configured as a manipulator.

FIG. 12 shows a holding arrangement configured as a manipulator 1200 with the holding arrangement having several rotational joints. The holding arrangement includes an arm 1201 which is mounted on a stand 1202 and can there be moved with rotational axes 1203 and 1204. Electric motors 1205 and 1206 are assigned to rotational axes 1203 and 1204, respectively. The arm 1201 is connected via a rotational joint 1207 to arm 1208. The arm 1208, in turn, holds an arm 1210 via a rotational joint 1209. On this arm 1210, an instrument receptacle unit 1212 is disposed on a rotational joint 1211 and has a unit for accommodating a tool in the form of an instrument holder 1213. The instrument holder 1213 holds a medical instrument in the form of a surgical tool 1220.

A handle 1214 is provided on the instrument receptacle unit 1212. An operator can control the manipulator 1200 with the handle 1214. Electric motors 1215, 1216 and 1217 are mounted on rotational joints 1207, 1209 and 1211, respectively. The stand 1202 is, in turn, disposed on a stand console 1218 and can there be rotated about a vertical axis 1219. With the handle 1214, an operator can move the instrument 1220, which is accommodated on the instrument holder 1213, in the directions indicated by arrows 1221, 1222, 1223 and 1224.

Angle transducers 1225, 1226, 1227 and 1228 are provided at the respective rotational joints of the manipulator 1200. The instantaneous position of the respective rotational joints can be detected utilizing the respective angle transducers 1225, 1226, 1227 and 1228. The signals of the angle transducers 1225, 1226, 1227 and 1228 are supplied to a control unit 1229 which controls the electric motors 1215, 1216 and 1217 for torque balancing in correspondence to the manner explained with respect to FIG. 11. This permits an operator to guide the manipulator 1200 force-free via the handle 1214 in correspondence to the directions indicated by the arrows 1221, 1222, 1223 and 1224.

Figure 13:
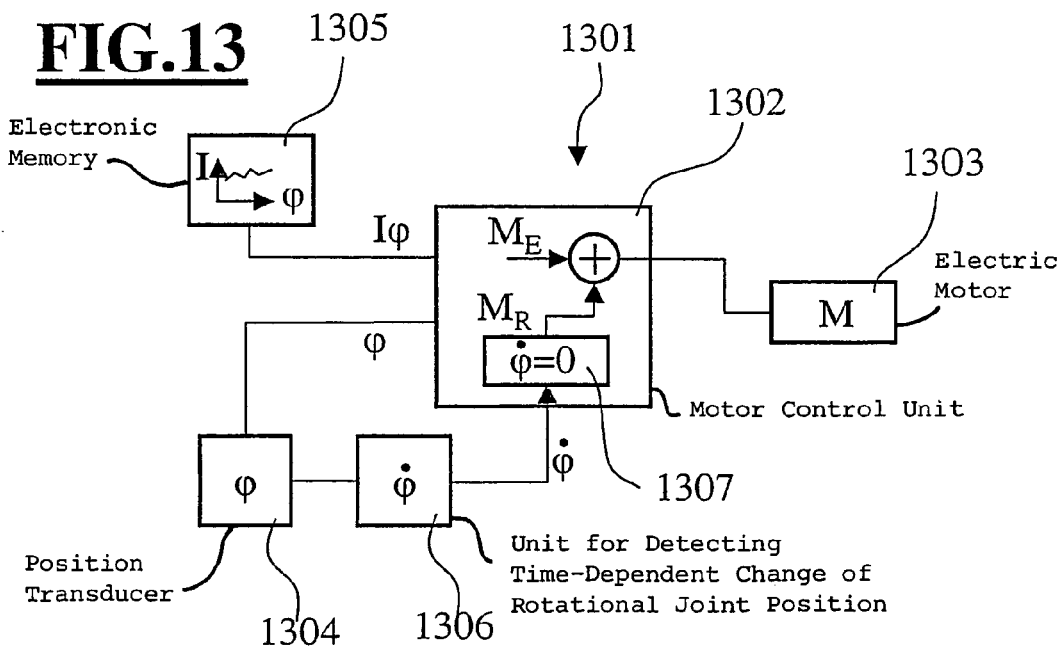
FIG. 13 is a schematic of a circuit arrangement with a control loop for controlling an electric motor in a rotational joint of the holding arrangement configured as the manipulator of FIG. 9; and, FIG. 14 is a circuit arrangement with control loops for controlling electric motors in several rotational joints of a holding arrangement.

FIG. 13 is a schematic of a circuit arrangement 1301 for controlling the electric motor 1303 in a rotational joint of the holding arrangement of FIG. 12 configured as a manipulator. The circuit arrangement 1301 is modified compared to FIG. 7 or FIG. 11.

The circuit arrangement 1301 includes a motor control unit 1302 which is connected to the electric motor 1303. The circuit arrangement 1301 includes a position transducer 1304 which supplies data as to the instantaneous position of the rotational joint having the electric motor 1303 to the control unit 1302. In correspondence to the circuit arrangement 701 of FIG. 7, the circuit arrangement 1301 includes an electronic memory 1305 wherein a current control curve is stored. The current control curve contains the data of a current for the electric motor on the particular rotational joint as a function of the rotational joint position. This current for the electric motor is needed for torque balancing. The current control curve can be stored, for example, as a mathematical function or as a value table. Here, it can be provided to interpolate, as needed, intermediate values by means of a suitable mathematical function. For an instantaneous rotational joint position, the motor control unit 1302 generates a motor control signal $M_E$ for torque compensation in the rotational joint having electric motor 1303.

As a difference with respect to the circuit arrangement 701 of FIG. 7, the circuit arrangement 1301 is additionally provided with a unit for detecting the time-dependent change of the rotational joint position 1306. The unit for detecting the time-dependent change of the rotational joint position 1306 is connected to the position transducer 1304. The unit determines the time-dependent change of the rotational joint position via a time-dependent derivative of the data as to the rotational joint position which is supplied from the position transducer 1304. As an alternative, it is, for example, also possible to detect the time-dependent change of the rotational joint position by evaluating the motor current in the electric motor 1303 of the corresponding rotational joint.

The data of the time-dependent change of the rotational joint position 1306 is likewise supplied to the motor control unit 1302. There, a closed control loop 1307 stores the detected time-dependent change of the rotational joint position as a control quantity. The control loop 1307 outputs a motor control signal $M_R$ as an actuating quantity. The control loop 1307 is configured as a PID control loop to which, as a set value, the value $\dot{\Phi}_{des}=0$ is pregiven as a value for a wanted time-dependent change of the rotational joint position. It is, however, noted that the control loop can also be configured in accordance with another control principle known to those skilled in the art.

Because of the selected desired value $\dot{\Phi}_{des}=0$, the motor control signal $M_R$ corresponds to a motor current in the electric motor 1303 which counters a displacement of the rotational joint.

In the motor control unit 1302, the motor control signal $M_R$, which is outputted by the control loop 1307, is superposed on the motor control signal $M_E$ for torque balancing in the rotational joint having electric motor 1303 at a given angular position.

An operator, who shifts the corresponding rotational joint, for example, with a handle 1214 shown in FIG. 12, perceives this counter action of the electric motor as a shift resistance corresponding to an inertial force. The shift resistance is dependent upon a displacement speed.

The dependency of the shift resistance on a shift speed can be adjusted to a desired value by selecting the time constant in the PID control loop.

By utilizing corresponding control loops, it is basically also possible to assign a desired shift resistance to a given shift speed.

The circuit arrangement 1301 makes possible to move an instrument, which is accommodated on the holding arrangement, in equilibrium about a rotational joint, for example, with the handle 1214 of FIG. 12 without the need for torques to be generated by the operator which would counter the torques which occur in the particular rotational joint because of a displacement of the mass center of gravity of the accommodated instrument. At the same time, with the movement of the handle, the operator perceives a touch-perceptible resistance which, for example, prevents that tremors of a human hand are transmitted to the instrument accommodated on the holding arrangement. Non-predefin-able forces and torques (for example, cutting forces and return forces when cutting tissue) must be developed for the manipulator by the operator. This is, however, desirable because, in this way, the operator has a real, touch-perceptible feedback without falsifying external forces.

Figure 14:
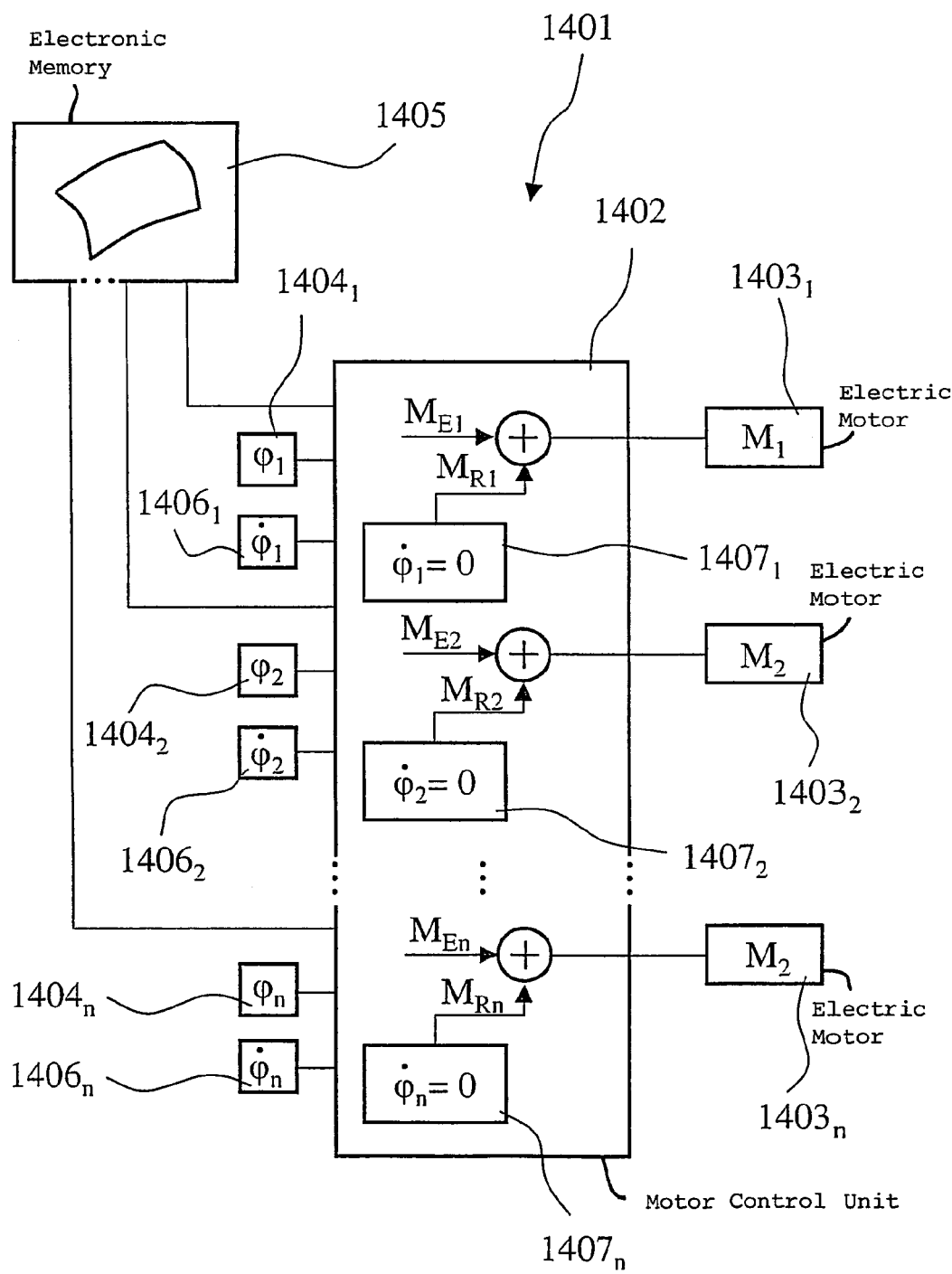

FIG. 14 shows a schematic of a further circuit arrangement 1401 for controlling several electric motors $1403_1$, $1403_2$, ... $1403_n$ which are arranged in corresponding rotational joints of a holding arrangement configured as a manipulator as explained basically with respect to FIG. 11. The circuit arrangement 1401 has a motor control unit 1402 which is connected to the electric motors $1403_1$, $1403_2$, ... $1403_n$ at the corresponding rotational joints whose rotational joint positions are detected by position transducers $1404_1$, $1404_2$, ... $1404_n$. In correspondence to the circuit arrangement 1101 of FIG. 11, the circuit arrangement 1401 includes an electronic memory wherein a multidimensional current control curve is stored which contains the data of a motor current for equilibrium $M_{E1}$, $N_{E2}$, ... $M_{En}$ for electric motors $1403_1$, $1403_2$, ... $1403_n$, for a given position of the rotational joints.

In contrast to the circuit arrangement 1101, units for detecting the time-dependent change of the position of the particular rotational joints $1406_1$, $1406_2$, ... $1406_n$ are provided in the circuit arrangement 1401. The units supply the data of a time-dependent change of the rotational joint position to the motor control unit 1402.

In the motor control unit 1402, this information is supplied as a control quantity to the control loops $1407_1$, $1407_2$, ... $1407_n$. These control loops output motor control signals $M_{R1}$, $M_{R2}$, ... $M_{Rn}$ as an actuating quantity. Corresponding to the circuit arrangement explained with respect to FIG. 13, each of the motor control signals $M_{R1}$, $M_{R2}$, ... $M_{Rn}$, counters the shift of the rotational joints to which the corresponding electric motors $1403_1$, $1403_2$, ... $1403_n$, are assigned.

In the motor control unit 1402, the motor control signals $M_{R1}$, $M_{R2}$, ... $M_{Rn}$, which are outputted by the control loops $1407_1$, $1407_2$, ... $1407_n$, are superposed on the motor control signals $M_{E1}$, $M_{E2}$, ... $M_{En}$ for torque balancing by electric motors $1403_1$, $1403_2$, ... $1403_n$.

With a manipulator as holding arrangement having several rotational joints, the circuit arrangement thereby makes it possible to guide an instrument via a suitable handle in equilibrium, that is, to move the same apparently force-free for an operator without, for example, the tremors of the human hand being transferred to the instrument. The rotational joints are driven by corresponding electric motors.

A holding arrangement, which is configured as a manipulator and which is controlled via a circuit arrangement shown in FIG. 11, thereby permits a precise tremor-free guidance of microsurgical instruments, especially injectors, endoscopes or laparoscopes. Basically, such a manipulator can be provided with an electronic drive in each axis of movement. The drive can be controlled (open loop and/or closed loop) in a suitable manner. With such a manipulator, implants, permanent pharmaceuticals, sensors, actuators or even detectors and the like can be precisely positioned on a patient.

Such a manipulator can also carry a probe head for measuring workpieces or a gripping work tool. It is basically also possible, with a corresponding manipulator, to pick up heavy instruments, items or tools which can then be fine-motorically moved by an operator. For example, especially, heavy items can be precisely positioned, fixed or assembled.

If an arm configuration is selected for the manipulator (which takes into account a weight compensation about corresponding rotational joints via a suitable mass distribution), then it is possible to utilize comparatively weak electric motors for adjusting a torque compensation in the axes of movement. This can also make possible a manual operation of the manipulator without support of electric motors. Especially, only the comparatively low torques of a weak electric motor have to be overcome.

For working with the manipulator, it can be provided to identify an item, which is to be picked up by the manipulator, via a barcode or by triggering a microchip and, in correspondence to a known mass distribution of the picked-up item, to then set suitable motor current control curves for torque compensation in the memory of a control unit assigned to the manipulator.

For the sake of completeness, it is noted that a corresponding workpiece or tool can be identified as an item, which is picked up by the manipulator, also by the identification. principle of automatic feed devices in machine tools in the forms of magazines or changers.

Compared to classic robot technology, the holding arrangement described affords the advantage that it does not require costly force-torque sensors. In this robot technology, complex sensor actuator controls for servo operation of robotic arms driven by motors must be used.

It is understood that the foregoing description is that of the preferred embodiments of the invention and that various changes and modifications may be made thereto without departing from the spirit and scope of the invention as defined in the appended claims.

What is claimed is:

1. A holding arrangement for an instrument including a medical-optical instrument, the holding arrangement comprising:
   at least one rotational joint which is subjected to a load torque by said instrument;
   said rotational joint having a first joint part and a second joint part which can be moved relative to the first joint part: and,
   an apparatus for balancing said load torque applied to said rotational joint;
   said apparatus including: an electric motor; a detecting unit for detecting a position of said rotational joint and for providing a signal representing a position value for said position of said rotational joint;
   said electric motor being combined with said detecting unit; and, said electric motor being connected to said second joint part by means of a shaft;
   a control unit for receiving said signal and assigning a motor current to said position value; and,
   said control unit outputting said motor current to said electric motor so as to cause said electric motor to generate a counter torque introduced into said second joint part of said rotational joint to balance said load torque applied to said rotational joint.

2. The holding arrangement of claim 1, said apparatus further comprising a brake assigned to said rotational joint.

3. The holding arrangement of claim 2, said apparatus further comprising a gear assembly for coupling said electric motor to said rotational joint.

4. The holding arrangement of claim 3, said rotational joint defining a rotational axis and said electric motor defining a drive axis offset relative to said rotational axis.

5. The holding arrangement of claim 4, wherein said detecting unit includes an encoder of said electric motor or a position transducer.

6. The holding arrangement of claim 1, wherein said rotational joint is a first rotational joint and said apparatus is a first apparatus and wherein said holding arrangement further comprises a second rotational joint and a second apparatus for balancing a second load torque caused by said instrument and applied to said second rotational joint.

7. The holding arrangement of claim 6, wherein said electric motor of said first apparatus is a first electric motor and said second apparatus includes a second electric motor; said control unit includes two control loops; and, each of said apparatus further comprises means for detecting a time-dependent change of the position of the rotational joint corresponding thereto and for supplying said time-dependent change to said control loops; and, said control loops output two motor currents for corresponding ones of said electric motors which counter the change of position of said rotational joints.

8. The holding arrangement of claim 1, wherein said instrument is taken up with an articulated parallelogram on a carrier arm.

9. The holding arrangement of claim 1, wherein said holding arrangement is configured as a manipulator for moving an instrument.

10. The holding arrangement of claim 9, wherein a handle is provided for moving said manipulator.

11. The holding arrangement of claim 1, said apparatus further comprising an electronic memory assigned to said control unit; and, said electronic memory having a curve of current as a function of rotational joint position or a table of current/rotational joint stored therein.

12. The holding arrangement of claim 11, said apparatus further comprising means for detecting a time-dependent change of the position of said rotational joint.

13. The holding arrangement of claim 12, wherein said control unit includes a closed control loop for receiving said time-dependent change of the position of said rotational joint; and, said control loop outputs a motor current for said electric motor at said rotational joint which counters said change of the position of said rotational joint.

14. The holding arrangement of claim 13, wherein said control unit superposes said motor current outputted by said control loop onto said motor current outputted by said control unit to balance said load torque applied to said rotational joint.

15. A holding arrangement for an instrument including a medical-optical instrument, the holding arrangement comprising:
   at least one rotational joint which is subjected to a load torque by said instrument; and,
   an apparatus for balancing said load torque applied to said rotational joint;
   said apparatus including: an electric motor; a detecting unit for detecting a position of said rotational joint and for providing a signal representing a position value for said position of said rotational joint; and, said electric motor being combined with said detecting unit;
   a control unit for receiving said signal and assigning a motor current to said position value;
   said control unit outputting said motor current to said electric motor so as to cause said electric motor to generate a counter torque to balance said load torque applied to said rotational joint;
   said apparatus further comprising a brake assigned to said rotational joint;
   said apparatus further comprising a gear assembly for coupling said electric motor to said rotational joint;
   said rotational joint defining a rotational axis and said electric motor defining a drive axis offset relative to said rotational axis;

said detecting unit including an encoder of said electric motor or a position transducer; and, an electronic memory assigned to said control unit; and, said electronic memory having a curve of current as a function of rotational joint position or a table of current/rotational joint stored therein.

16. The holding arrangement of claim 15, said apparatus further comprising means for detecting a time-dependent change of the position of said rotational joint.

17. The holding arrangement of claim 16, wherein said control unit includes a closed control loop for receiving said time-dependent change of the position of said rotational joint; and, said control loop outputs a motor current for said electric motor at said rotational joint which counters said change of the position of said rotational joint.

18. The holding arrangement of claim 17, wherein said control unit superposes said motor current outputted by said control loop onto said motor current outputted by said control unit to balance said load torque applied to said rotational joint.

19. A holding arrangement for an instrument including a medical-optical instrument, the holding arrangement comprising:

at least one rotational joint which is subjected to a load torque by said instrument; and, an apparatus for balancing said load torque applied to said rotational joint, said apparatus including: an electric motor; a detecting unit for detecting a position of said rotational joint and for providing a signal representing a position value for said position of said rotational joint; and, said electric motor being combined with said detecting unit;

a control unit for receiving said signal and assigning a motor current to said position value; and, said control unit outputting said motor current to said electric motor so as to cause said electric motor to generate a counter torque to balance said load torque applied to said rotational joint;

said rotational joint being a first rotational joint and said apparatus being a first apparatus and wherein said holding arrangement further comprises a second rotational joint and a second apparatus for balancing a second load torque caused by said instrument and applied to said second rotational joint;

said electric motor of said first apparatus being a first electric motor and said second apparatus including a second electric motor; said control unit including two control loops; and, each of said apparatus further comprising means for detecting a time-dependent change of the position of the rotational joint corresponding thereto and for supplying said time-dependent change to said control loops; and, said control loops outputting two motor currents for corresponding ones of said electric motors which counter the change of position of said rotational joints.

20. A method for determining a current control curve for adjusting an equilibrium state in a holding arrangement which includes: at least one rotational joint which is subjected to a load torque by said instrument; and, an apparatus for balancing said load torque applied to said rotational joint; said apparatus including: an electric motor; a detecting unit for detecting a position of said rotational joint and for providing a signal representing a position value for said position of said rotational joint; and, said electric motor being combined with said detecting unit; a control unit for receiving said signal and assigning a motor current to said position value; said control unit outputting said motor current to said electric motor so as to cause said electric motor to generate a counter torque to balance said load torque applied to said rotational joint; the method comprising the steps of:

rotating said rotational joint about said rotational axis thereof utilizing said electric motor;

determining the current demand of said electric motor required to effect the movement of said rotational joint about said rotational axis;

determining the instantaneous position of said rotational joint; and, storing said current demand as a current control curve in an electronic memory as a function of the position of said rotational joint.

21. The method of claim 20, comprising the further steps of:

determining the current demand needed to move said rotational joint in a first direction utilizing said electric motor;

moving said rotational joint in said first direction utilizing said electric motor;

determining the current demand needed to move said rotational joint utilizing said electric motor in a second direction opposite to said first direction; and, moving said rotational joint utilizing said electric motor in said second direction opposite to said first direction.

22. The method of claim 21, comprising the further steps of:

computing a first mean value for the current demand needed to move said rotational joint in said first direction;

computing a second mean value for the current demand needed to move said rotational joint in said second direction; and, storing said first and second mean values in said electronic memory in dependence upon the position of said rotational joint.

23. The method of claim 22, comprising the further step of rotating said rotational joint by a rotational angle of $|\Phi|\leq\Pi$ or $|\Phi|\leq\Pi/2$ or $|\Phi|\leq\Pi/4$ utilizing said electric motor in order to determine said current control curve.

24. A method for adjusting an equilibrium state in a holding arrangement which includes: at least one rotational joint which is subjected to a load torque by said instrument; and, an apparatus for balancing said load torque applied to said rotational joint; said apparatus including: an electric motor; a detecting unit for detecting a position of said rotational joint and for providing a signal representing a position value for said position of said rotational joint; and, said electric motor being combined with said detecting unit; a control unit for receiving said signal and assigning a motor current to said position value; said control unit outputting said motor current to said electric motor so as to cause said electric motor to generate a counter torque to balance said load torque applied to said rotational joint; the method comprising the steps of:

determining an instantaneous position of said rotational joint; and, supplying current to said electric motor in correspondence to a current control curve stored in a memory with said current control curve assigning a current value for torque compensation to said instantaneous position of said rotational joint.

25. The method of claim 24, the method comprising the further steps of:
    determining an instantaneous change of the position of said rotational joint; and,
    outputting a current to said electric motor which counters the change of the position of said rotational joint.

26. A method for determining a current control curve for adjusting a state of equilibrium in a holding arrangement which includes: at least one rotational joint which is subjected to a load torque by said instrument; and, an apparatus for balancing said load torque applied to said rotational joint; said apparatus including: an electric motor; a detecting unit for detecting a position of said rotational joint and for providing a signal representing a position value for said position of said rotational joint; and, said electric motor being combined with said detecting unit; a control unit f or receiving said signal and assigning a motor current to said position value; said control unit outputting said motor current to said electric motor so as to cause said electric motor to generate a counter torque to balance said load torque applied to said rotational joint; said rotational joint being a first rotational joint and said apparatus being a first apparatus; a second rotational joint and a second apparatus for balancing a second load torque caused by said instrument and applied to said second rotational joint; said electric motor of said first apparatus being a first electric motor and said second apparatus including a second electric motor; the method comprising the steps of:
    detecting the position of said first rotational joint;
    with the position of said first rotational joint known, moving said second rotational joint about its axis utilizing said second electric motor;
    determining the current demand of said second electric motor needed to move said second rotational joint;
    determining the instantaneous position of said second rotational joint;
    storing the current demand in dependence upon the position of said second rotational joint as a first current control curve in an electronic memory;
    thereafter, and for the known position of said second rotational joint, moving said first rotational joint about its axis utilizing said first electric motor;
    determining the current demand of said first electric motor needed for the movement of said first rotational joint;
    determining the instantaneous position of said first rotational joint; and,
    storing the determined current demand in dependence upon the position of said first rotational joint in said electronic memory as a second current control curve.

27. The method of claim 26, comprising the further steps of:
    detecting the position of a third rotational joint;
    with the respective positions of said first and second rotational joints known, moving said third rotational joint about its axis utilizing a third electric motor assigned to said third rotational joint;
    determining the current demand of said third electric motor needed to move said third rotational joint;
    determining the instantaneous position of said third rotational joint; and,
    storing said current demand of said third rotational joint in dependence upon the position of said first rotational joint and upon the position of said second rotational joint in an electronic memory as a current control curve.

28. A method for adjusting a state of equilibrium in a holding arrangement which includes: at least one rotational joint which is subjected to a load torque by said instrument; and, an apparatus for balancing said load torque applied to said rotational joint; said apparatus including: an electric motor; a detecting unit for detecting a position of said rotational joint and for providing a signal representing a position value for said position of said rotational joint; and, said electric motor being combined with said detecting unit; a control unit for receiving said signal and assigning a motor current to said position value; said control unit outputting said motor current to said electric motor so as to cause said electric motor to generate a counter torque to balance said load torque applied to said rotational joint; said rotational joint being a first rotational joint and said apparatus being a first apparatus; a second rotational joint and a second apparatus for balancing a second load torque caused by said instrument and applied to said second rotational joint; said electric motor of said first apparatus being a first electric motor and said second apparatus including a second electric motor; the method comprising the steps of:
    determining an instantaneous position of said first rotational joint;
    determining an instantaneous position of said second rotational joint;
    supplying current to said first electric motor and said second electric motor in correspondence to a current control curve stored in a memory; and,
    wherein said current control curve assigns each of said first and second electric motors a current value for torque compensation in correspondence to the respective ones of said instantaneous positions.

29. The method of claim 28, wherein said holding arrangement further includes a third rotational joint and a third electric motor assigned to said third rotational joint, the method comprising the further steps of:
    determining an instantaneous position of said third rotational joint;
    supplying current to said third electric motor in correspondence to a current control curve stored in a memory; and,
    wherein said current control curve assigns each of said first, second and third electric motors a current value for torque compensation in correspondence to respective ones of said instantaneous positions.

* * * * *

UNITED STATES PATENT AND TRADEMARK OFFICE
CERTIFICATE OF CORRECTION

PATENT NO.        : 7,109,678 B2
APPLICATION NO.   : 10/879037
DATED             : September 19, 2006
INVENTOR(S)       : Martin Kraus et al.

It is certified that error appears in the above-identified patent and that said Letters Patent is hereby corrected as shown below:

Title Page:
Item (75) Inventors:
delete:
"Martin Kraus, Hüttlingen (DE);
Hartmut Gärtner, Oberkochen (DE);
Martin Poxleitner, Königsbronn (DE);
Michael Wirth, Aalen (DE);
Alfons Abele, Scwäbisch Gmünd (DE);
Roland Brenner, Wallhausen (DE);
Norbert Sporer, Wielenbach (DE);
Matthias Hähnle, Munich (DE)"

and substitute
-- Roland Brenner, Wallhausen (DE);
Alfons Abele, Schwäbisch Gmünd (DE);
Hartmut Gärtner, Oberkochen (DE);
Martin Poxleitner, Königsbronn (DE);
Michael Wirth, Aalen (DE);
Norbert Sporer, Wielenbach (DE);
Matthias Hähnle, Munich (DE);
Martin Kraus, Hüttlingen (DE) -- therefor.

TITLE PAGE, ITEM (12)
DELETE "Kraus, et al." and substitute -- Brenner, et al. --.

Column 4:
Line 29: delete "dependence-upon" and substitute
-- dependence upon -- therefor.

Column 6:
Line 66: delete "305-which" and substitute -- 305 which -- therefor.

Column 8:
Line 38: delete "known-position" and substitute -- known position -- therefor.

UNITED STATES PATENT AND TRADEMARK OFFICE
CERTIFICATE OF CORRECTION

PATENT NO.      : 7,109,678 B2
APPLICATION NO. : 10/879037
DATED           : September 19, 2006
INVENTOR(S)     : Martin Kraus et al.

It is certified that error appears in the above-identified patent and that said Letters Patent is hereby corrected as shown below:

Column 9:
Line 36: delete "$0 \leq \Phi \leq 2\Pi$" and substitute -- $0 < \Phi < 2\Pi$ -- therefor.

Column 12:
Line 19: delete "$N_{E2}$," and substitute -- $M_{E2}$, -- therefor.

Column 13:
Line 18: delete "fication." and insert -- fication -- therefor.

Signed and Sealed this

Sixteenth Day of January, 2007

JON W. DUDAS
*Director of the United States Patent and Trademark Office*